(12) United States Patent  
Florin et al.

(10) Patent No.: US 6,833,923 B2
(45) Date of Patent: Dec. 21, 2004

(54) METHOD FOR 3D OBJECT-SCANNING

(75) Inventors: Ernst-Ludwig Florin, Gaiberg (DE); Heinrich J. K. Hörber, Weiltingen (DE); Ernst H. K. Stelzer, Meckesheim (DE)

(73) Assignee: Europaisches Laboratorium fur Molekularbiologie (EMBL), Heidelberg (DE)

( * ) Notice: Subject to any disclaimer, the term of this patent is extended or adjusted under 35 U.S.C. 154(b) by 375 days.

(21) Appl. No.: 09/987,764

(22) Filed: Nov. 15, 2001

(65) Prior Publication Data

US 2002/0063868 A1 May 30, 2002

Related U.S. Application Data

(60) Provisional application No. 60/249,282, filed on Nov. 17, 2000.

(51) Int. Cl.$^7$ ............................ G01B 11/24; G01B 11/14
(52) U.S. Cl. ........................................ 356/601; 356/625
(58) Field of Search ................................ 356/600–601, 356/625

(56) References Cited

PUBLICATIONS

Pralle et al., "Three Dimensional High–Resolution Particle Tracking for Optical Tweezers by Forward Scattered Light", *Microscopy Research and Technique*, 44:378–386 (1999).

Hörber et al., "Photonische Kraftmikroskopie", *Physikalische Blätter*, 56 (2000) Nr. 5, pp. 41–44.

Pralle et al., "Sphingolipid–Cholesterol Rafts Diffuse as Small Entities in the Plasma Membrane of Mammalian Cells", *The Journal of Cell Biology*, vol. 148, No. 5, Mar. 6, 2000, pp. 997–1007.

Pralle et al., "Photonic Force Microscopy: A new Tool Providing New Methods to Study Membranes at the Molecular Level", *Single Mol.*, 1 (2000) 2, 129–133.

Jeney, et al., "Use of Photonic Force Microscopy to Study Single–Motor–Molecular Mechanics", *Methods in Molecular Biology*, vol. 164, pp. 91–108.

*Primary Examiner*—Frank G. Font
*Assistant Examiner*—Amanda Merlino
(74) *Attorney, Agent, or Firm*—Rothwell, Figg, Ernst & Manbeck

(57) ABSTRACT

A method for detecting an object and/or an object's ambience and/or an object's inner space using a scanning particle trapped within a trapping potential. The trapping potential is configured within a position range defined relative to the object or a reference point in a first position determining stage which is associated with a first order of magnitude. In a second position determining stage, which is associated with an order of magnitude less than that of the first order of magnitude, the scanning particle trapped within the trapping potential moves more or less freely in three-dimensions while scanning subjected to the trapping potential to scan the scan volume. A plurality of scanning particle positions assumed as a consequence of scanning are detected within the scan volume.

65 Claims, 4 Drawing Sheets

METHOD FOR 3D OBJECT-SCANNING

This non-provisional application claims the benefit of U.S. Provisional Application No. 60/249,282 filed Nov. 17, 2000.

BACKGROUND OF THE INVENTION

1. Field of Invention

The present invention relates to a method for detecting an object and/or the area immediately surrounding an object and/or the interior of an object with regard to physical and/or chemical and/or biological problems. More particularly, the invention relates to a method that uses a scanning particle within a potential trap to scan the object or the area immediately surrounding or its interior wherein at least one scanning-dependent position of the scanning particle is detected.

2. Description of Related Art

As is well known in the art, photons carry momentum equal to the product of photon wavelength and Planck's action quantum. The momentum carried by the photons can be transferred to matter. A. Ashkin ("Acceleration and trapping particles by radiation pressure", Physical Review Letters 24(4), pp 156–159 [1970]) was able to show that small particles within a substantially collimated laser beam do move towards the zone of the strongest field (highest intensity). By using a slightly divergent laser beam pointing away from the center of the earth, Ashkin compensated for gravity and trapped glass particles having diameters of approximately 20 μm in a position wherein the force of radiation pressure balances gravity. See A. Ashkin, J M Dziedzik, "Optical levitation by radiation pressure", Applied Physics Letters, 19(8), pp 283–285 [1971]. A further experiment showed that two laser beams pointing at one another create a 3-D potential that traps the particle in all three spatial coordinates. See A. Ashkin, J M Dziedzik, "Observation of radiation pressure trapping of particles by alternating light beams", Physical Review Letters 54(2), pp 145–147, [1985]. Furthermore, a highly focused laser beam using lenses of high NA (small f/numbers) was shown to be able to retain particles in aqueous media in all three spatial coordinates. See A. Ashkin, J M Dziedzik, J E Bjorkholm, S Chu "Observation of a single-beam gradient force optical trap for dielectric particles", Optics Letters 11(5), pp 288–290 [1986]. When the laser beam is moved, the particles follow the focal zone of the trapping beam.

Based on such work, measuring devices commonly referred to as optical tweezers were built into microscopes to measure small forces that occur during the interaction between proteins. See K. Visscher, G J Brakenhoff, "Single beam optical trapping integrated in a confocal microscope for biological applications", Cytometry 12, pp 486–491 [1991]. In such measurements, it is extremely critical to use sensors that detect the particle position relative to the geometric focal point of the laser trapping beam. Cameras may be used in the simplest cases. See L. Malmqvist, H M Hertz, "Trapped particle microscopy", Optics Communication 94, pp 19–24 [1992]. Malmqvist and Hertz built a near field microscope having optical tweezers wherein a trapped particle scatters light and is considered a light source passing through an object to be observed. The light source approaches objects to be observed within a few nanometers. In this method, the object is irradiated by the near field induced by the particle rather than the far field of the microscope lens. The image is recorded as a shadow in the far field.

Another method uses a quasi-heterodyne interferometer to measure particles at the geometrical focus of the trapping beam. See W Denk, W W Webb, "Optical measurement of picometer displacements of transparent microscopic objects" Applied Optics, 29(16), pp 2382–2391 [1990]. The light scattered forward and the unscattered light interfere in a diode so that a one-dimensional position of the particle is measured relative to the geometric focus of the trapping beam. In principle, the accuracy of determining the position of the particle depends only on the signal-to-noise ratio of the detection method. It should be noted that noise is meant in the terms of the stochastic phenomenon rather than in the acoustic sense.

Some conventional methods use cameras as well as quadrant photodiodes, cathode beam cameras, CCD or CID cameras, and spatially resolving secondary electron multipliers, for example, to determine the positions of small particles to sub-pixel accuracy. See M J Saxton and K Jacobson, "Single-particle tracking: applications to membrane dynamics", Annual Review of Biophysics and Biomolecular Structures 26, pp 373–399 [1997].

Ghislain and Webb describe an instrument wherein a glass bit is first caught using optical tweezers and is then moved over a surface. The above mentioned interferometer detects the object excursion. See L P Ghislain, WW Webb, "Scanning force microscope based on an optical trap", Optics Letters, 18(19), pp 1678–1680 [1993]. The topological change is inferred from the change in scattering intensity.

A force microscope based on the principle of the optical tweezers is disclosed by U.S. Pat. No. 5,445,011 wherein a probe is deflected microscopically and the excursion is determined. The instrument disclosed by U.S. Pat. No. 5,445,011 may be less effective than a conventional force microscope and may not offer the desired advantages since instrument's resolution is limited by thermal vibrations of the probe. See A L Stout, W W Webb, "Optical force microscopy", Methods in Cell Biology 55, pp 99–116 [1998].

In a scientific paper presented by the Applicants it was shown that the position of a trapped fluorophore-marked latex particle can be determined using the intensity of the fluorescence. See E L Florin, J K H Hörber, E H K Stelzer, "High-resolution axial and lateral position sensing using two-photon excitation of fluorophores by a continuous-wave Nd/YAG laser", Applied Physics Letters 69(4), pp 446–448 [1996]. The field intensity applied to a particle in optical tweezers changes with its position in the point spread function. Also, the fluorescence intensity varies as a function of particle position along the optical axis. The axial position can be determined at an accuracy better than 8 nm.

Regarding fluorescence detection of the axial position of a particle trapped in optical tweezers, the particle should be trapped, not at the geometric focus but, and depending on particle size, behind the geometric focus as seen in the direction of the beam. See T Wohland, A Rosin, E H K Steizer, "Theoretical determination of the influence of the polarization on forces exerted by optical tweezers", Optik, 102(4), pp 180–190 [1996]. As a rule, this will be the case with known optical tweezers because of the radiation pressure on the particle. Because of the different interaction intensity, even in axially symmetric potentials, it is possible to determine the particle position along the optical axis. See A Pralle, M Prummer, E-L Florin, E H K Steizer, J K H Hörber "Three-dimensional high-resolution position tracking for optical tweezers by forward scattered light:" Microscopy Research and Techniques 44(5), pp 378–386 [1999].

Another conventional method used to determine a particle position within an optical potential is based on the analysis of an interference pattern derived, for example, from a plane conjugate to an image plane or Fourier plane. See A Pralle, M Prummer, E-L Florin, E H K Stelzer, J H K Hörber, "Three-dimensional high-resolution particle tracking for optical tweezers by forward scattered light", Microscopy Research Techniques 44(5), pp 378–386, [1999]. An interference pattern between unscattered laser light and laser light scattered at the particle is analyzed by a quadrant diode and the position of the particle constituting the scattering center is determined relative to a geometric focus of the optical tweezers.

The forces of the photons, i.e., optical force, acting on a particle trapped by optical tweezers may be calibrated by analyzing the thermal noise of the particle positions within the optical tweezers' trapping potential. See E-L Florin, A Pralle, E H K Stelzer, J K H Hörber, "Photonic force microscope calibration by thermal noise analysis", Applied Physics A, pp 75–78 [1998]. Moreover, based on the statistical analysis of the Brownian motion of the particle within the trapping potential of the optical tweezers, the local viscosity describing the interaction with a medium surrounding the particle may be determined. See A Pralle, E-L Florin, E H K Stelzer, J K H Hörber, "Local viscosity probed by photonic force microscopy", Applied Physics A, 66, pp 71–73 [1998].

A photon, i.e., optical, force microscope having optical tweezers and determining the axial position of a particle trapped in a trapping potential of the optical tweezers by detecting the fluorescence intensity produced from two-photon stimulation is described in a recently published report. See E-L Florin, A Pralle, J H K Hörber, E H K Steizer, "Photonic force microscope based on optical tweezers and two-photon excitation for biological applications", Journal of Structural Biology, 119, pp 202–211 [1997]. By scanning biological probes using the trapped particle, namely a tiny latex sphere, and while recording the fluorescence intensity caused by two photons, two-dimensional images are produced.

Moreover optical tweezers may also be used to manipulate analytes as disclosed in WO96/41154 wherein a tiny sphere is attached to the particular analyte and the analyte is then moved over the sphere or forces are exerted on the analyte. Also, a particle trapped by the optical tweezers is bound, using a membrane protein, to a neurite surface of a neuron in order to observe diffusive displacement of the membrane protein along the surface. See A Pralle, M Prummer, E-L Florin, E H K Stelzer, J K H Hörber, "Three-dimensional high-resolution position tracking for optical tweezers by forward scattered light" Microscopy Research Techniques 44(5), pp 378–386 [1999]. In such a method, the particle trapped by the optical tweezers' trapping potential always adheres to the neurite surface using the membrane protein because the variations in position due to thermal noise are insufficient under the experimental conditions to break the bond between the particle and the surface.

In conventional methods, the Brownian, i.e., thermal, motion of the particle trapped by the optical tweezers' trapping potential is constantly a limiting factor. Thermal-noise position fluctuations of the particle heretofore could rarely be analyzed. However, the thermal-noise position fluctuations could be analyzed when relating to specific problems such as, for example, when determining the local viscosity or calibrating the trapping potential.

Therefore, the above-described conventional scanning methods have merely provided information regarding a mean particle position and resulted in an inherent limit on resolution due to thermal noise because the Brownian motion of the scanned particle within the trapping potential gives rise to fluctuations in the detected position signal, such as, for instance, a fluorescence signal or a scattered signal.

SUMMARY OF THE INVENTION

It is an object of this invention to overcome the drawbacks of the above-described conventional methods. It is also an object of this invention to use particle position fluctuations within the trapping potential to scan the object and/or the area immediately surrounding the object and/or the object interview. Rather than only considering the short-term variations of the position signal as being noise, the method of this invention ascribes such variations of particle position as thermally induced position noise within the potential applied by the optical tweezers. Further, the invention uses the fact that within the observation time interval, the particle moves through a volume element of the volume defined by the optical tweezers, which is basically a trap, with a dwell-time or dwell probability or probability density depending on the value of the potential. The particle position fluctuations of the particle, i.e., scanning particle being trapped in the trapping potential, may be thermally induced and/or induced by other mechanisms. In the latter case, the resulting particle position fluctuations are generally superimposed on the thermally induced particle position fluctuations. Besides noise or fluctuation motions of the scanning particle, other scanning motions applied to the particle may also be considered. It should be noted that the invention is not limited to using the optical tweezers or light radiation to generate the trapping potential. The trapping potential may also be produced magnetically and/or electrostatically and/or using non-optical, electromagnetic AC fields.

According to one aspect of this invention in a first position-determining stage associated with a first order of magnitude, the trapping potential is implemented in a position zone defined relative to the object or a reference point. In a second position determining stage associated with a second order of magnitude less than the first, the scanning particle trapped in the trapping potential scans within a scan volume associated with the position zone essentially in a free, 3-D manner while remaining subject to the trapping potential. The scanning particle scans the scan volume in such manner that a plurality of positions assumed by the particle during scanning of the interior of the volume is detected. The position zone of the trapping potential relative to the object may be changed by implementing a change of the position zone of the trapping potential and/or by changing the position of the object in order to scan a region transcending the scan volume and/or region of the trapping potential.

Conventional scanning is carried out, such as, for example, when regarding a surface, within one position determining stage. In particular, conventional scanning is carried out by positioning the trapping potential next to position zones which constitute a matrix of discrete scanning or sampling points. As a result, the matrix spacings must be selected to be small to obtain high resolution. Furthermore, the thermal noise motions of the scanning particles inherently limit resolution. In contrast to this conventional scanning, this invention performs the scanning motion proper on the basis of the substantially unbounded 3-D scanning motion, such as, for example, the Brownian motion of the scanning particle, over the scanning region. The scanning motion is carried out subjected to the trapping potential and possibly with the interactions with a neighboring object. However, the scanning particle may not be bound to the object, such as, for example, by chemical or molecular bonding or another close-range chemical bond, because otherwise the scan volume, which is determined by the trapping potential, and, where applicable by the location of the position zone of the trapping potential relative to any object, cannot be scanned in 3D.

By analyzing the scanning motions, and the position noise where applicable of the scanning particle, the invention makes it possible to detect an object, in particular the surface zone of the object, the area immediately surrounding the object and also the interior of the object. Furthermore, the motions or position noise may be used to survey the 3D trapping potential, to determine the point spread function, e.g. of the optical system, and to detect regions which, while within the point spread function, are unattainable to the particle for mechanical, electric, magnetic, chemical, biochemical, biological or other reasons. This feature allows conclusions about basic physical values, for example, thermodynamic, rheologic or tribologic values. Because the measurement, i.e., the scanning, takes place in three dimensions and because the trapping potential need not meet special conditions, anisotropic values may also be ascertained and in particular, non-harmonic potentials can be used as the trapping potentials.

As a rule, the first order of magnitude shall be microscopic and the second order of magnitude shall be sub-microscopic. A microscopic scanning of a sample according to a conventional scanning method may be, according to the invention, supplemented by the detection of the sub-microscopic scanning motion of the scanning particle in the scan volume. Unlike the state of the art, however, the invention does not ascertain the mean particle position in the trapping potential, but instead individual volume elements are resolved by being scanned by the particle at different sites in the scan volume and possibly at different sites within an object. Accordingly, a far-field resolution of a mean position of a scanning particle is supplemented by sub-microscopic resolution. If during the first stage of position determination the trapping potential is shifted into another position zone relative to the object or reference point, then the full scan volume shall have been shifted relative to the object or reference point. If it is desired that the sub-microscopic scanning results, i.e., from the scanning motion of the scanning particle in the particular scan volume, be consolidated into a total scanning result for the various microscopic position zones, then appropriately, the accuracy at which the particular position zone is determined or determinable and the accuracy at which the position of the scanning particle can be determined in the scan volume should be of the same order of magnitude, preferably of the order of nanometers or even picometers. A particular position zone of the trapping potential relative to the object or the reference point may be defined by a given focal point characterizing the trapping potential and/or by a mean trapping beam position.

It should be noted that the trapping potential may be configured in a microscopic process, preferably optically, in the position zone, and that the scanning particle scans the scan volume as a consequence of a sub-microscopic process.

A conventional optical tweezers design may be used to optically configure the trapping potential. An example of a sub-microscopic process implementing scanning is the interaction between the scanning particle and a heat bath, that is, the sub-microscopic interactions leading to the thermal position noise, i.e., Brownian motion, of the scanning particle. Other equally applicable sub-microscopic processes are fluctuations of the trapping potential and mechanical, in particular acoustic effects on the scanning particle. The scanning motions of the scanning particle in the scan volume based on the sub-microscopic process are detected by an appropriate position-determining or motion sensing system and in this manner are made available for analysis with respect to the particular problems.

Preferably the process initiating the scanning by the scanning particle of the scan volume is such that the motion of the particle within the scan volume is random or nearly random on a time scale that is longer than an auto-correlation time and preferably corresponds to a predetermined statistic, for example, the Maxwell-Boltzmann statistic. 3D structures are imaged especially effectively using such "random" or "near random" scanning.

To obtain information about the object and/or the area immediately surrounding the object and/or the interior of the object, the motion of the scanning particle shall be detected in especially appropriate manner over a detection time interval exceeding the autocorrelation time so that a plurality of scanning particle positions detected at different times can be statistically analyzed with respect to the particular problem. If, however, additional or alternative data are desired about local object properties and/or the area immediately surrounding the object and/or the interior of the object and/or diffusive behavior of the object, then alternatively or additionally the scanning particle motion can be detected using a detection time interval which is shorter than the autocorrelation time.

The scanning particle's scan of the scan volume may be based, as already mentioned, on the thermally induced changes in position of the particle. By setting a corresponding temperature and/or the trapping potential with respect to intensity and function, it is possible to control the thermally induced scan regarding the scanning particle's amplitudes of motion. Even when using other mechanisms to induce the particle's scanning motions, thermally induced changes in position of the particle contributes to scanning the volume by the particle.

Further, the scanning of the scan volume by the scanning particle may be based on electromagnetically induced changes in position of the particle or on the contribution from electromagnetically induced particle changes of position. Particle changes in position may be induced by changing an external electromagnetic field interacting with the scanning particle. Depending on the kind of scanning particle, magnetic or electric, i.e., electrostatic fields may be used that are periodically changed by using noise generators so that time-varying forces are applied to the article to induce the changes in position.

Compared with such external fields, however, preferably the external electromagnetic field should at least be co-generating the trapping potential. As a trapping potential, one can identify a mean or effective potential that describes the interaction between the scanning particle and the external electromagnetic field on a time scale associated with the first stage of position determination. The time scale does not resolve the changes in the external magnetic field causing the changes in position of the particle. Preferably, if the trapping potential is generated using focused laser beams, then there is the possibility of mechanically vibrating or shaking an optical component in the path of the laser beam, such as, for example, a focusing optics, in order to exert, by using the trapping potential, corresponding forces on the scanning particle, thereby changing its position.

Further, the intensity of the laser beam may be changed in order to change the magnitude of the trapping potential, and thereby the forces exerted by the potential on the particle, to induce changes in the position of the particle. Such changes in laser beam intensities may be implemented using modulators known in the optics field, such as for example, an electro-optical or an acousto-optical modulator, or by correspondingly controlling the laser, i.e., laser modulation by laser pumping or by driving the electric or light power of the laser, e.g. a diode laser. A chopper may also be used for short-term and repeated interruption of the laser beam.

It should also be noted that placing such controls on the scanning particle using the trapping potential is not a part of the first stage of position determination because the particle on the time-average sees a mean or effective potential at the position zone defined relative to the object or a reference point. The mean trapping potential, which also may be denoted as an average potential, determines a mean position zone. The mean trapping potential, either alone or with the object to be tested, and possibly with the structure of an object support, or a sample chamber, defines a scan volume that encloses all space elements attainable by the scanning particle trapped in the trapping potential. The probability of the particle being in a particular volume element depends on the potential function and the potential value. The spatial extension or reach of the mean or effective potential may be characterized by an effective reach value, which basically may be considered to correspond to a rms reach value calculated from instantaneous reach values of a real trapping potential which changes with respect to strength, relative location or other parameters on a time scale associated with the second stage of position determination.

In another aspect of the invention, the scanning of the scan volume by the scanning particle is based on mechanically induced changes in the scanning particle position. Mechanically induced changes in the scanning particle position may at least contribute to that scanning. Foremost, acoustically induced changes in position are applicable. An object support and/or a sample chamber containing the object may be loaded mechanically, in particular acoustically, to cause the changes in position, such as, for example, using piezoelectric acoustic generators.

A key feature, but not the only, of the invention is the detection of positions assumed by the scanning particle inside the scan volume, such as, for example, relative to a particle rest position within the trapping potential or, preferably, relative to an unambiguous reference point of the trapping potential itself. Thus, in the case of a light optical trapping potential, the reference point preferably would be a geometric focus. Several options exist with which to detect these positions. Preferably, the detection of the scanning particle positions shall be electromagnetic, in particular optical. Illustratively, the detection of the scanning particle positions within the scan volume is detected using electromagnetic radiation emanating from the particle and/or transmitted through the particle. If the trapping potential is generated based on electromagnetic radiation, the electromagnetic radiation detected for purposes of particle position determination may be related to the radiation contributing to the trapping potential, or may be entirely independent of such. Illustratively, the trapping potential may be generated using a laser beam of a first wavelength and the scanning particle position ascertained by interaction of the particle with a laser beam of another wavelength. However, ideally, the interaction between the electromagnetic radiation generating the trapping potential with the scanning particle is used to determine, either directly or indirectly, the scanning particle's position within the scan volume.

The electromagnetic radiation emanating from the scanning particle may include radiation scattered or reflected by the particle. Moreover, the electromagnetic radiation emanating from the particle may include recombination radiation based on atomic and/or molecular transitions, preferably induced by a multi-photon process. Therefore, luminescent radiation emanating from the scanning particle, in particular, fluorescence and/or phosphorescence, may be detected to determine the particle's position, in particular, the axial position. Reference is made in this respect to the above discussions on position detection using the scanning particle's fluorescent radiation.

The position is detected at especially high resolution by analyzing an interference pattern of electromagnetic radiation depending on the particle position within the scan volume. Illustratively, the electromagnetic radiation may be a forward-scattered laser beam of optical tweezers. Specific reference is made here to the previously discussed report by Pralle et al "Three-dimensional high-resolution particle tracking for optical tweezers by forward scattered light."

As discussed above, the trapping potential may be generated using optical radiation, in particular laser radiation, that interacts with the scanning particle. Preferably, electromagnetic radiation resulting from the interaction is detected to determine the scanning particle's position. In most cases, optical radiation resulting from the interaction will be detected.

If an object beyond the range of the trapping potential is to be detected for example, a macroscopic object in part or in full, the trapping potential's position zone may be changed relative to the object by changing the potential's position zone and/or by changing the position of the object. In the case of optical tweezers, for example, a microscopic lateral displacement of the trapping potential and accordingly the scanning particle relative to the object may be implemented by tilting a laser beam providing the optical tweezers into one or two planes. Preferably, the laser beam is tilted within a primary plane or an optically conjugate Fourier plane of a lens element or a specific lens used to focus the laser beam. Moreover, the microscopic lateral displacement of the trapping potential and the scanning particle relative to the object may be implemented by displacing the object itself. Regarding a microscopic axial displacement of the trapping potential and accordingly the scanning particle relative to the object, the displacement may be implemented by moving an optical component, in particular a lens element, part of a lens or the like along an optic axis characterizing the laser beam propagation. However, microscopic axial displacement of the trapping potential and accordingly the scanning particle relative to the object may also be accomplished by axially displacing the object.

Furthermore, a region extending beyond the scan volume and/or the reach of the trapping potential may be scanned by superposing on the scan by the particle associated with the second order of magnitude within the scan volume a higher ranked scan associated with the first order of magnitude. This can be done by changing the trapping potential's position zone; accordingly, therefore, the trapping potential may be shifted from position zone to position zone, preferably at spacings between the position zones corresponding to the first order of magnitude, whereby the scan by the scanning particle within the scan volume implemented at the second order of magnitude takes place in each position zone. The position zones of the tapping potential may be configured in a matrix in order for instance to detect a macroscopic object.

However, such a scanning method becomes problematic if the object has a solid surface that is impervious to a scanning particle which may be frequently the case. In such an instance, a plain, matrix-wise scanning at the first order of magnitude may entail that the scanning particle cannot accompany the shifting of the trapping potential because it hits a barrier and therefore drops out of the range or influence of the trapping potential. To remedy this situation, one may, according to the invention, perform the higher-ranked scanning in accordance with a scanning strategy, according to which the position zone of the trapping potential is changed by taking into account a scanning result or scanning results associated with the second order or magnitude possibly using known object data.

Besides detecting or covering extended objects, the invention also allows observing an object and/or the area immediately surrounding the object and/or the interior of the object in order to detect locally over a time interval the changes in the object and/or the object area immediately surrounding the object and/or the interior of the object. Accordingly, the trapping potential's position zone is preserved through the time interval so as to repeatedly detect within it the plurality of positions assumed by the scanning particle within the scan volume and to come to a conclusion about the changes that took place.

Regarding many problems or questions, it may be appropriate to change, at a particular position zone, the associated scan volume, for example, to enlarge or reduce a volume within which the scanning particle is present at a given probability. Such a change in scan volume may be implemented by changing the potential's field intensity and/or the function of said trapping potential.

Basically no restrictions apply regarding the kind of scanning particles being used. The scanning particle must be selected in relation to the particular trapping potential in order that it can be kept trapped by its interaction with the trapping potential. It is frequently appropriate to use a spherical and/or fluorescent scanning particle. In the case of a fluorescent scanning particle, the above mentioned detection of position may be attained by using particle fluorescence. The scanning particle may be metallic or a high-grade metallic particle, a latex particle, a glass particle, a nano-particle, possibly a quantum dot, or a heterogeneous or homogeneous collection of any such particles.

A scanning particle designed for a particular problem or provided with a certain functionality in view of the particular problem may be used in order to broaden the applicability of the above described method. Foremost, a scanning particle may be used that exhibits special interaction properties relative to the object. In this manner, it is possible to investigate for instance the surface properties and/or deposit characteristics and/or electromagnetic features and/or mechanical traits of an object more closely.

In general, the method of the invention is appropriate for investigating interaction potentials in the vicinity of an object, the mechanics of an object, such as, for example, its vibrations, the chemical nature of an object, in particular boundary surface properties. Another significant application of the proposed method is cellular biology. This enumeration is not limiting. A pertinent field of application furthermore is the detection, that is scanning, of nano-structures. It is believed that such application may substantially contribute to the increasingly important field of nano-engineering.

Depending on application, an appropriate selection shall be made of the trapping potential, its generation, and of the detection of the particle position. If an optical trapping potential is selected, the particular light wavelength will be chosen in relation to the measurements being taken, especially with respect to the kind of object. Regarding the many biological applications, the 1,064 nm line of an Nd:YVO$_4$ laser is especially appropriate. Other wavelengths apply to other applications. For example, when testing solids, a wavelength should be selected that, if possible, is transparent for the solid, for example, a semiconductor. This feature is particularly significant when imaging semiconductor structures, where the measurements call for a wavelength matched to the semiconductor's energy gap so that the absorption in the semiconductor is minor.

Using a light wavelength transparent for the test object not only facilitates the detection of the particle position, for instance, by using an interference pattern of scattered radiation, but it also precludes undue heating, and even destruction of the object.

It may be appropriate, depending on the measuring configuration and the object to be investigated, to simultaneously scan using several particles so that several trapped scanning particles are used within one common trapping potential. If a position is detected from the scanning particle's emitted fluorescence, then the scanning particles may be chosen to emit at different wavelengths. As a result, the individual particle positions may be detected in a simple manner.

To detect the positions of the scanning particle position or scanning particles within the scan volume, in many applications it will suffice to determine the positions only summarily, possibly in such manner that the scanning result allows inferring the probability of the particle having dwelt in one or several volume elements of the scan volume. In such a case, it is not necessary to monitor the motion of the particle within the scan volume, nor is it mandatory called for in this invention. Still in many other applications, it will be significant to monitor the particle motion within the scan volume and to resolve it. For the latter purpose, both the position and the time at which the particle was in that position must be detected, that is, the particle motion must be detected and resolved both in space and in time.

The invention also relates to equipment to carry out the above described method. The equipment of the invention includes apparatus to generate a trapping potential in a desired position zone associated with a first order of magnitude and a detection system to detect the positions of at least one scanning particle which is trapped within the trapping potential and which carries out substantially free 3D motions subjected to the trapping potential within a scan volume associated to the position zone, the detected positions being associated with a second order of magnitude which is less than the first.

These and other objects of the present invention will be described in or be apparent from the following description of the preferred embodiments.

BRIEF DESCRIPTION OF THE DRAWINGS

For the present invention to be easily understood and readily practiced, preferred embodiments will now be described, for purposes of illustration and not limitation, in conjunction with the following figures.

DETAILED DESCRIPTION OF PREFERRED EMBODIMENTS

Figure 1:
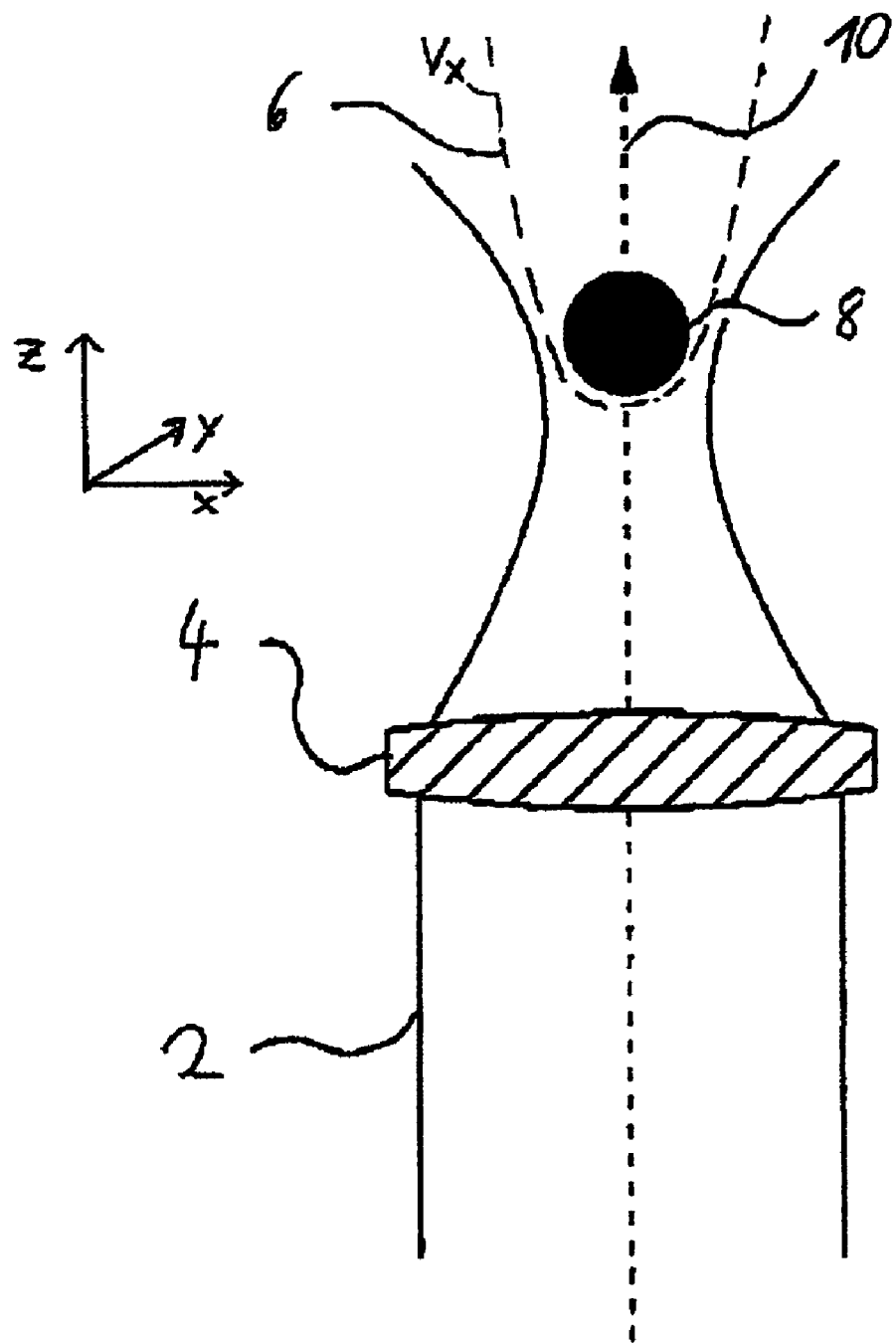
FIG. 1 is a schematic diagram of a particle trapped by optical tweezers according to a preferred embodiment of the invention.

FIG. 1 is a schematic diagram of a particle trapped by optical tweezers. A light beam 2 of sufficiently high intensity, for example, a laser beam, is focused through a lens element or objective 4, so that a three-dimensional trapping potential, i.e., the trapping potential 6, is generated in the vicinity of the geometric focus. FIG. 1 also shows an exemplary potential function VX (dashed lines), i.e. an exemplary dependency of the trapping potential at the scanning particle's rest position from the x-coordinate, i.e. in the x-direction. It should be noted that the function of the trapping potential is not critical in implementing the method of the invention. The trapping potential may be harmonic or non-harmonic. Although a harmonic potential function is typically used.

The scanning particle 8 is trapped in the trapping potential and remains trapped therein long-term due to the dielectric interaction with the trapping potential. The position zone, i.e., the microscopic position, of the trapping potential 6 and accordingly of the scanning particle 8 is defined by the position and alignment of the lens 4 relative to the optical axis 10 which defines the propagation of the laser beam 2. When the laser beam 2 is tilted, the trapping potential 6 is displaced laterally in the x- and/or y-direction as is particle 8. Shifting the lens 4 along the optical axis 10 axially displaces the trapping potential 6 and accordingly particle 8 along the optical axis.

Because of thermal, and any other, fluctuations or effects, the scanning particle 8 moves sub-microscopically within the trapping potential 6 independently of any microscopic movement of the trapping potential, possibly obtained by tilting of the laser beam 2 or changing the lens position. Because of sub-microscopic motions, the scanning particle moves within a three-dimensional volume called a scan volume which is defined by the trapping potential 6 and any spatial boundary conditions, i.e., for example, boundary surfaces of an object or object support. Aside from the boundary surfaces, the scan volume is not uniquely defined or bounded, at least in terms of sub-microscopic fluctuating motions of the particle. For such submicroscopic fluctuating motions, it may be the case that only dwell probabilities of the scanning particle can be obtained. In principle, a strong fluctuation may move the particle out of the trapping potential and outside the scan volume, which may entail loss of the scanning particle. Appropriately, one considers as the scan volume such a volume, in which the scanning particle resides at a predetermined probability of 50% or 90%, to provide two examples.

Figure 2:
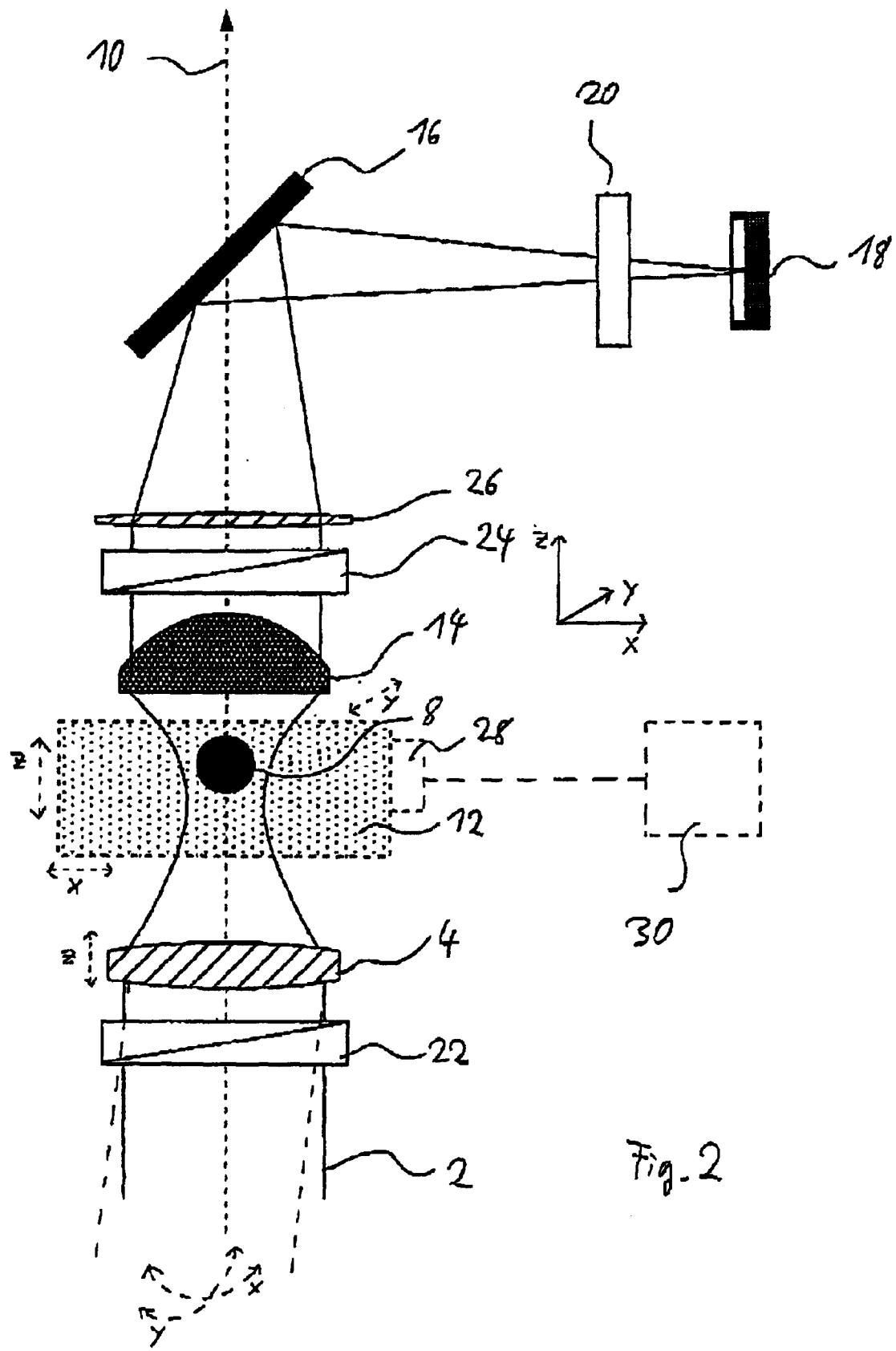
FIG. 2 is a schematic diagram illustrating an apparatus having optical tweezers which allow various implementations of the method of the invention.

FIG. 2 shows the optical tweezers of FIG. 1 complemented by further components in order to attain detection of an object and/or the area surrounding the object and/or the interior of the object. As shown by FIG. 2, the light beam 2, which exhibits a suitable intensity and preferably is provided as a laser beam, is focused through the lens 4 into a probe chamber 12. According to the point spread function of lens 4, the focused light, jointly with the properties of the scanning particle 8, generates the 3D trapping potential for the particle 8. Light scattered forward by the particle 8 is collimated through a condenser lens 14. The collimated light is projected, preferably focused, through a deflecting device, in particular a deflecting mirror 16, onto a spatially sensitive detector 18, for instance a quadrant photo-diode. A light changing unit 20 behind the probe chamber 12, jointly with a light changing unit 22 in front of the probe chamber, allows matching the light properties to the detector 18. The light intensity and/or its polarization are adjustable. Appropriate light changing units in the form of passive components such as neutral density filters, dielectric interference filters, polarizers, polarizing beam splitters or prisms such as Wollaston prisms and/or in the form of active components such as acousto-optic or electro-optic modulators and the like may be used. In the embodiment of FIG. 2, the light changing unit 22 as well as an additional light changing unit 24 in the optical detection path are each in the form of a Wollaston prism. A tube lens 26 is furthermore used in the optical detection path.

The scanning particle 8 is selectively displaced within the probe chamber on a microscopic scale by positioning the latter and/or by changing the angle of incidence of the laser beam 2 on the lens 4 and/or by shifting the lens 4 along the optical axis 10. This feature is indicated in FIG. 2 by the arrows showing the controlled particle position coordinate (x, y and z).

Figure 3:
FIG. 3 is an example of a measuring or detection result obtained using the apparatus of FIG. 2 for scanning a particle optically trapped in an aqueous solution.

Sub-microscopic changes in position of the scanning particle 8 caused, for example, by thermal noise, are detected by the detector 18. A spatial distribution of the scanning particle 8 within the trapping potential is determined by repeatedly detecting the instantaneous particle position over a substantial time interval which is longer than a correlation time. FIG. 3 shows an approximately ellipsoidal surface of equal dwell probability of a particle optically trapped in an aqueous solution. The dwell probability of the particle being within the volume bounded by the surface is approximately 80%. If the scanning particle is situated inside the object or in the ambience of an object and if the particle motion in restricted by the object, then it will scan only the zones accessible to it in view of its interaction with the object. In the first place, mechanical interactions of the particle with the object or a structure within the reach of the particle may prevent access of the particle to certain zones. Thus, the particle cannot trivially reach zones situated behind a structure opaque to it. Furthermore, other physical, for example, electrical, chemical, and biological interactions may take place between the scanning particle and the object, which restrict the particle's scanning motions or at least affect its probability of dwell within the volume accessible to it.

Figure 4:
FIG. 4 is an example of a measuring or detection result obtained using the apparatus of FIG. 2 for scanning a particle held by optical tweezers in an agar gel.

FIG. 4 illustrates such a restriction on the scanning motion of a scanning particle by an object. Surfaces of equal dwell probability of a 200 nm diameter scanning particle are shown, which is optically held in an agar gel. The probability of the center of the scanning particle being within the volume defined by the surface is about 80%. Unscanned zones correspond to non-aqueous, i.e., solid segments of the object.

The scanning motion of the scanning particle also may be induced in other ways. In dashed lines, FIG. 2 indicates a acoustic transducer 28 connected to a noise generator 30. The transducer 28 transmits acoustic energy into the probe chamber 12 to implement sub-microscopic scanning motions of the scanning particle 8.

In another way, sub-microscopic scanning motions of the particle are implemented via the trapping potential. For example, the laser beam 2 can be modulated. To the extent the modulation affects the position detection by the detector 18, the effect of changing the trapping potential, for example, on an interference pattern imaged on the detector 18, may be taken into account during the position analysis.

If local changes of an object are to be observed, one may repeatedly record scanning results over a substantial time interval at a given microscopic position of the trapping potential, for example, to detect an object's volume change as a function of time. In this manner, for example, changes in biological cells may be observed.

Frequently however, object detection may relate to microscopic distances. This feature can be implemented by a scanning action superposed on the submicroscopic scanning action by appropriately changing the position zone of the trapping potential. Preferably, this microscopic scanning action takes into account extant information, in particular, previous test results, in order to determine those zones which subsequently should be scanned. In other words, the extant information is fed back into further scanning.

The scanning results substantially depend on the duration of scanning. If the dwell site of the scanning particle is detected at a scanning rate of which the reciprocal is longer or at least just as long as an autocorrelation time characteristic of the sub-microscopic particle motion, then the interpretation of the test results will be governed by the particle's diffusive behavior. If on the other hand, the dwell site of the scanning particle is detected at a scanning rate of which the reciprocal is shorter than the shortest autocorrelation time relative to the scanning particle's submicroscopic motion, then information may be obtained regarding the particle's speed or mobility and conditions affecting this speed or mobility. In this manner, information may be gathered concerning the local viscosity of a viscous medium.

The magnitude of the correlation time depends on the submicroscopic process inducing the particle's submicroscopic motion, on the kind of trapping potential and the kind of interaction of the particle with its ambience. In the case of a thermal fluctuations based submicroscopic particle motion of a spherical particle of radius p caught in a harmonic trapping potential moving in a medium of viscosity $\eta$, the correlation time $\tau$ will be $$\tau = y/\kappa = 6\pi\eta p\kappa$$

where $\kappa$ is the potential's spring constant and $y$ is the damping factor of the particle motion based on Stokes' friction in the viscous medium. See Pralle et al, "Local viscosity probed by photonic force microscopy".

Based, for instance, on the design shown in FIG. 2, the method of the invention may be used to scan an object's surfaces. In a further preferred application, an object's cavities are sensed, that is regions wherein an ambient medium, for instance an aqueous solution or air, and thereby also the scanning particle, is free to move. Moreover, a scanning particle provided with special functionality may be used which for example, exhibits certain properties with respect to the object interaction, for instance, with respect to surfaces bounding object cavities. As a result, information can be secured which transcends mere conventional scanning information.

Further, the invention allows a scanning of surfaces approximately in the manner known from tunnel and force microscopy. Contrary to the conventional case however, test specimens also may be investigated which are mounted between glasses in the conventional manner of optical microscopy because the scanning particle is trapped by the trapping potential in non-mechanical manner. Therefore objects also may be investigated from the inside without destroying them.

In summary the invention relates to a method for detecting an object and/or an object's ambience and/or an object's inner cavity or interior using a scanning particle trapped in a trapping potential. The invention proposes that, in a first position determining stage which is associated with a first order of magnitude, the trapping potential be configured within a position zone defined relative to the object or a reference point, and that in a second position determining stage associated with an order of magnitude less than that associated with the first position determining stage, the scanning particle trapped in the trapping potential implements an essentially free three-dimensional scanning motion while subjected to the trapping potential and scans the scan volume in such manner that a plurality of particle positions within the scan volume assumed on account of scanning shall be detected.

What is claimed is:

1. A method for detecting features of an object comprising:
    scanning at least one of the object, an area immediately surrounding the object, and an interior of the object, wherein a scanning particle trapped within a trapping potential performs the scan, said scanning being effected by:
        configuring the trapping potential in a position zone defined relative to one of the object and a reference point in a first position determining stage associated with a first order of magnitude, and
        performing a substantially free three-dimensional scan within a scan volume associated with the position zone using the scanning particle trapped within and controlled by the trapping potential in a second position determining stage associated with a second order of magnitude smaller than the first order of magnitude of the first position determining stage; and
    detecting a plurality of positions assumed by the scanning particle while scanning the scan volume, wherein the features of the object detected are at least one of physical, chemical, and biological.

2. The method according to claim 1, wherein the first order of magnitude is microscopic and the second order of magnitude is sub-microscopic.

3. The method according to claim 2, wherein the trapping potential is configured by a microscopic process in the position zone and the scanning particle sub-microscopically scans the scan volume based on a sub-microscopic process.

4. The method according to claim 3, wherein the microscopic process is an optical process.

5. The method according to claim 1, wherein the scanning of the scan volume by the scanning particle is performed such that a motion of the scanning particle within the scan volume is one of random and near-random on a time scale that is longer than an auto-correlation time.

6. The method according to claim 5, wherein the motion of the scanning particle is detected during a detection interval that exceeds the auto-correlation time interval in order to attain at least one of a plurality of uncorrelated or nearly uncorrelated scanning particle positions detected at different points in time, information about the object, the area surrounding the object, and the interior of the object.

7. The method according to claim 5, wherein the motion of the scanning particle is detected during a detection time interval corresponding to or shorter than the auto-correlation time in order to attain information about at least one of the object, the area surrounding the object, the interior of the object, and a diffusive behavior of the scanning particle.

8. The method according to claim 5, wherein said motion of the scanning particle corresponds to a given statistics.

9. The method according to claim 8, wherein said statistics is Maxwell-Boltzmann statistics.

10. The method according to claim 1, wherein the scanning of the scan volume by the scanning particle is based, at least in the sense of a contribution to the scanning, on thermally induced changes in the particle position.

11. The method according to claim 1, wherein the scanning of the scan volume by the scanning particle is based, at least in the sense of a contribution to the scanning, on electromagnetically induced changes in position of the scanning particle, wherein the change of position of the scanning particle is induced by changing an external electromagnetic field interacting with the scanning particle.

12. The method according to claim 11, wherein the external electromagnetic field is a field co-generating the trapping potential and the trapping potential is an effective potential defining interaction of the scanning particle with the external electromagnetic field on a time scale associated with the first position determining stage.

13. The method according to claim 1, wherein the scanning of the scan volume by the scanning particle is based, at least in the sense of a contribution to the scanning, on mechanically or acoustically induced position changes of the scanning particle.

14. The method according to claim 13, wherein at least one of an object support bearing the object and a probe chamber containing the object are loaded mechanically or acoustically in order to change the position of the scanning particle.

15. The method according to claim 1, wherein electromagnetic radiation emanating from and/or passing through the scanning particle is detected to determine the position of the scanning particle within the scan volume.

16. The method according to claim 15, wherein the electromagnetic radiation emanating from the scanning particle includes radiation scattered or reflected by the scanning particle.

17. The method according to claim 15, wherein the electromagnetic radiation emanating from the scanning particle includes recombination radiation based on atomic and/or molecular transitions associated with the scanning particle.

18. The method according to claim 17, wherein said recombination radiation is induced by a multi-photon process.

19. The method according to claim 1, wherein an electromagnetic radiation interference pattern is analyzed to detect the position of the scanning particle within the scan volume, wherein the interference pattern depends on the position of the scanning particle.

20. The method according to claim 1, wherein the trapping potential is generated using optical or laser radiation interacting with the scanning particle.

21. The method according to claim 20, wherein electromagnetic radiation is detected to ascertain the position of the scanning particle within the scan volume, wherein said electromagnetic radiation results from an interaction of the optical or laser radiation with the scanning particle.

22. The method according to claim 1, wherein the position zone of the trapping potential relative to the object is changed by changing at least one of the position zone of the trapping potential and the object position.

23. The method according to claim 22, wherein a scanning of a region transcending at least one of the scan volume and the range of the trapping potential is performed by changing the position zone of the trapping potential.

24. The method according to claim 1, wherein a change of any one of the object, the area immediately surrounding the object, and the interior of the object is detected over a time interval of change, wherein the position zone of the trapping potential is maintained during the time interval of change, and a plurality of assumed positions of the scanning particle is detected within the scan volume during the time interval of change.

25. The method according to claim 1, further comprising the step of changing at least one of a potential field intensity and potential function of the trapping potential in order to change the scan volume associated with a given position zone.

26. The method according to claim 1, wherein a particle is used as the scanning particle which is at least one of spherical and fluorescent.

27. The method according to claim 1, wherein one of a metal particle, a high-grade metal particle, a latex particle, a glass particle, a nano-particle, and a quantum dot are used as the scanning particle.

28. The method according to claim 1, wherein a scanning particle having special interacting properties relative to the object is used.

29. The method according to claim 1, wherein several scanning particles are used within a common trapping potential.

30. The method according to claim 1, wherein the features of the object refer to at least one of the object, the area immediately surrounding the object and the interior of the object.

31. The method according to claim 1, wherein said scanning is further effected by:
    changing the position zone of the trapping potential relative to the object by changing at least one of the position zone of the trapping potential and the position of the object, in order to scan a region transcending at least one of the scan volume and the range of the trapping potential.

32. The method according to claim 31, wherein the region transcending the scan volume is scanned by superposing on the scan of the scanning particle within the scan volume associated with the second order of magnitude a higher-ranking scan by changing the position zones of the trapping potential associated with the first order of magnitude.

33. The method according to claim 32, wherein the higher-ranking scan is carried out according to a scanning strategy wherein the position zone of the trapping potential is changed while taking into account at least one scanning result associated with the second order of magnitude.

34. A method for detecting features of an object comprising:
    scanning at least one of the object, an area immediately surrounding the object, and an interior of the object, wherein a scanning particle trapped within a trapping potential performs the scan and at least one particle position is detected; said scanning being effected by:
        configuring the trapping potential in a position zone defined relative to one of the object and a reference point in a first position determining stage associated with a first order of magnitude;
        performing a substantially free three dimensional scan within a scan volume associated with the position zone using the scanning particle trapped within and controlled by the trapping potential in a second position determining stage associated with a second order of magnitude smaller than the first order of magnitude of the first position determining stage; and changing the position zone of the trapping potential relative to the object by changing at least one of the position zone of the trapping potential, the position of the object in order to scan a region transcending at least one of the scan volume and a range of the trapping potential, wherein the features of the object detected are at least one of physical, chemical, and biological.

35. The method according to claim 34, wherein the region transcending the scan volume is scanned by superposing on the scan of the scanning particle within the scan volume associated with the second order of magnitude a higher-ranking scan by changing the position zones of the trapping potential associated with the first order of magnitude.

36. The method according to claim 35, wherein the higher-ranking scan is carried out according to a scanning strategy wherein the position zone of the trapping potential is changed while taking into account at least one scanning result associated with the second order of magnitude.

37. The method according to claim 34, wherein the first order of magnitude is microscopic and the second order of magnitude is sub-microscopic.

38. The method according to claim 37, wherein the trapping potential is configured by a microscopic process in the position zone and the scanning particle sub-microscopically scans the scan volume based on a sub-microscopic process.

39. The method according to claim 38, wherein said microscopic process is an optical process.

40. The method according to claim 34, wherein the scanning of the scan volume by the scanning particle is performed such that a motion of the scanning particle within the scan volume is one of random and near-random on a time scale that is longer than an auto-correlation time.

41. The method according to claim 40, wherein the motion of the scanning particle is detected during a detection interval that exceeds the auto-correlation time interval in order to attain at least one of a plurality of uncorrelated or nearly uncorrelated scanning particle positions detected at different points in time, information about the object, the area surrounding the object, and the interior of the object.

42. The method according to claim 40, wherein the motion of the scanning particle is detected during a detection time interval corresponding to or shorter than the auto-correlation time in order to attain information about at least one of the object, the area surrounding the object, the interior of the object, and a diffusive behavior of the scanning particle.

43. The method according to claim 40, wherein said motion of the scanning particle corresponds to a given statistics.

44. The method according to claim 43, wherein said statistics is Maxwell-Boltzmann statistics.

45. The method according to claim 34, wherein the scanning of the scan volume by the scanning particle is based, at least in the sense of a contribute to the scanning, on thermally induced changes in the particle position.

46. The method according to claim 34, wherein the scanning of the scan volume by the scanning particle is based, at least in the sense of a contribute to the scanning, on electromagnetically induced changes in position of the scanning particle, wherein the change of position of the scanning particle is induced by changing an external electromagnetic field interacting with the scanning particle.

47. The method according to claim 46, wherein the external electromagnetic field is a field co-generating the trapping potential and the trapping potential is an effective potential defining interaction of the scanning particle with the external electromagnetic field on a time scale associated with the first position determining stage.

48. The method according to claim 34, wherein the scanning of the scan volume by the scanning particle is based, at least in the sense of a contribute to the scanning, on mechanically or acoustically induced position changes of the scanning particle.

49. The method according to claim 48, wherein at least one of an object support bearing the object and a probe chamber containing the object are loaded mechanically or acoustically in order to change the position of the scanning particle.

50. The method according to claim 34, wherein electromagnetic radiation emanating from and/or passing through the scanning particle is detected to determine the position of the scanning particle within the scan volume.

51. The method according to claim 50, wherein the electromagnetic radiation emanating from the scanning particle includes radiation scattered or reflected by the scanning particle.

52. The method according to claim 50, wherein the electromagnetic radiation emanating from the scanning particle includes recombination radiation based on atomic and/or molecular transitions associated with the scanning particle.

53. The method according to claim 52, wherein said recombination radiation is induced by a multi-photon process.

54. The method according to claim 34, wherein an electromagnetic radiation interference pattern is analyzed to detect the position of the scanning particle within the scan volume, wherein the interference pattern depends on the position of the scanning particle.

55. The method according to claim 34, wherein the trapping potential is generated using optical or laser radiation interacting with the scanning particle.

56. The method according to claim 55, wherein electromagnetic radiation is detected to ascertain the position of the scanning particle within the scan volume, wherein said electromagnetic radiation results from an interaction of the optical or laser radiation with the scanning particle.

57. The method according to claim 34, wherein the change of the position zone of the trapping potential relative to the object is implemented by changing at least one of the position zone of the trapping potential and the object position.

58. The method according to claim 34, wherein a change of any one of the object, the area immediately surrounding the object, and the interior of the object is detected over a time interval of change, wherein the position zone of the trapping potential is maintained during the time interval of change, and a plurality of assumed positions of the scanning particle is detected within the scan volume during the time interval of change.

59. The method according to claim 34, further comprising the step of changing at least one of a potential field intensity and potential function of the trapping potential in order to change the scan volume associated with a given position zone.

60. The method according to claim 34, wherein a particle is used as the scanning particle which is at least one of spherical and fluorescent.

61. The method according to claim 34, wherein one of a metal particle, a high-grade metal particle, a latex particle, a glass particle, a nano-particle, and a quantum dot are used as the scanning particle.

62. The method according to claim 34, wherein a scanning particle having special interacting properties relative to the object is used.

63. The method according to claim 34, wherein several scanning particles are used within a common trapping potential.

64. The method according to claim 34, wherein the features of the object refer to at least one of the object, the area immediately surrounding the object and the interior of the object.

65. An apparatus to implement the method claimed in claim 1, comprising:

a system generating a trapping potential at a desired position zone associated with a first order of magnitude; and a detection system detecting the positions of at lease one scanning particle which is trapped within the trapping potential and carries out a substantially free three-dimensional motion under the effect of the trapping potential within a scanning volume associated with the position zone, the detected positions being associated with a second order of magnitude less than the first order of magnitude.

* * * * *